(12) United States Patent
Kieval et al.

(10) Patent No.: US 8,594,794 B2
(45) Date of Patent: Nov. 26, 2013

(54) BAROREFLEX ACTIVATION THERAPY WITH INCREMENTALLY CHANGING INTENSITY

(75) Inventors: Robert S. Kieval, Medina, MN (US); Eric Grant Lovett, Mendota Heights, MN (US); Alejandro Covalin, Hopkins, MN (US)

(73) Assignee: CVRx, Inc., Minneapolis, MN (US)

(*) Notice: Subject to any disclaimer, the term of this patent is extended or adjusted under 35 U.S.C. 154(b) by 1264 days.

(21) Appl. No.: 12/175,415

(22) Filed: Jul. 17, 2008

(65) Prior Publication Data

US 2009/0030478 A1 Jan. 29, 2009

Related U.S. Application Data

(60) Provisional application No. 60/951,660, filed on Jul. 24, 2007.

(51) Int. Cl.
*A61N 1/00* (2006.01)

(52) U.S. Cl.
USPC .............................................. 607/44

(58) Field of Classification Search
USPC .................................................. 607/2, 44
See application file for complete search history.

(56) References Cited

U.S. PATENT DOCUMENTS

| | | | |
|---|---|---|---|
| 3,309,924 A | 3/1967 | Alexander et al. |
| 3,522,811 A | 8/1970 | Schwartz et al. |
| 3,645,267 A | 2/1972 | Hagfors |
| 3,650,277 A | 3/1972 | Sjostrand et al. |
| 3,835,864 A | 9/1974 | Rasor et al. |
| 3,870,051 A | 3/1975 | Brindley |
| 3,943,936 A | 3/1976 | Rasor et al. |
| 4,014,318 A | 3/1977 | Dockum et al. |
| 4,114,628 A | 9/1978 | Rizk |
| RE30,366 E | 8/1980 | Rasor et al. |
| 4,256,094 A | 3/1981 | Kapp et al. |
| 4,323,073 A | 4/1982 | Ferris |
| 4,331,157 A | 5/1982 | Keller, Jr. et al. |
| 4,481,953 A | 11/1984 | Gold et al. |
| 4,525,074 A | 6/1985 | Murakami |
| 4,531,943 A | 7/1985 | Van Tassel et al. |
| 4,551,862 A | 11/1985 | Haber |
| 4,573,481 A | 3/1986 | Bullara |
| 4,586,501 A | 5/1986 | Claracq |
| 4,590,946 A | 5/1986 | Loeb et al. |

(Continued)

FOREIGN PATENT DOCUMENTS

| | | |
|---|---|---|
| WO | WO 97/18856 | 5/1997 |
| WO | WO 98/02209 | 1/1998 |

(Continued)

OTHER PUBLICATIONS

Bilgutay et al., "Baropacing, a New Concept in the Treatment of Hypertension," from *Baroreceptors and Hypertension Proceedings of an International Symposium*, (Nov. 1965), p. 425-437.

(Continued)

*Primary Examiner* — Mark W Bockelman
(74) *Attorney, Agent, or Firm* — Patterson Thuente Pedersen, P.A.

(57) ABSTRACT

The present invention provides systems, devices, and methods for using the same for activating (stimulating) the baroreflex system of a patient using a baroreflex activation system with incrementally changing therapy intensity by sensing/monitoring/interpreting sensed data.

19 Claims, 7 Drawing Sheets

(56) References Cited

U.S. PATENT DOCUMENTS

| | | |
|---|---|---|
| 4,640,286 A | 2/1987 | Thomson |
| 4,641,664 A | 2/1987 | Botvidsson |
| 4,664,120 A | 5/1987 | Hess |
| 4,682,583 A | 7/1987 | Burton et al. |
| 4,702,254 A | 10/1987 | Zabara |
| 4,709,690 A | 12/1987 | Haber |
| 4,711,251 A | 12/1987 | Stokes |
| 4,719,921 A | 1/1988 | Chirife |
| 4,739,762 A | 4/1988 | Palmaz |
| 4,762,130 A | 8/1988 | Fogarty et al. |
| 4,762,820 A | 8/1988 | Gavras |
| 4,770,177 A | 9/1988 | Schroeppel |
| 4,791,931 A | 12/1988 | Slate |
| 4,800,882 A | 1/1989 | Gianturco |
| 4,803,988 A | 2/1989 | Thomson |
| 4,813,418 A | 3/1989 | Harris |
| 4,825,871 A | 5/1989 | Cansell |
| 4,828,544 A | 5/1989 | Lane et al. |
| 4,830,003 A | 5/1989 | Wolff et al. |
| 4,860,751 A | 8/1989 | Callaghan |
| 4,867,164 A | 9/1989 | Zabara |
| 4,881,939 A | 11/1989 | Newman |
| 4,886,062 A | 12/1989 | Wiktor |
| 4,887,608 A | 12/1989 | Mohl et al. |
| 4,917,092 A | 4/1990 | Todd et al. |
| 4,960,133 A | 10/1990 | Hewson |
| 4,967,159 A | 10/1990 | Manes |
| 4,969,458 A | 11/1990 | Wiktor |
| 4,972,848 A | 11/1990 | Di Domenico et al. |
| 4,987,897 A | 1/1991 | Funke |
| 5,025,807 A | 6/1991 | Zabara |
| 5,040,533 A | 8/1991 | Fearnot |
| 5,078,736 A | 1/1992 | Behl |
| 5,086,787 A | 2/1992 | Grandjean et al. |
| 5,092,332 A | 3/1992 | Lee et al. |
| 5,113,859 A | 5/1992 | Funke |
| 5,113,869 A | 5/1992 | Nappholz et al. |
| 5,117,826 A | 6/1992 | Bartelt et al. |
| 5,134,997 A | 8/1992 | Bennett et al. |
| 5,144,960 A | 9/1992 | Mehra et al. |
| 5,154,170 A | 10/1992 | Bennett et al. |
| 5,154,182 A | 10/1992 | Moaddeb |
| 5,158,078 A | 10/1992 | Bennett et al. |
| 5,170,802 A | 12/1992 | Mehra |
| 5,181,911 A | 1/1993 | Shturman |
| 5,199,428 A | 4/1993 | Obel et al. |
| 5,203,326 A | 4/1993 | Collins |
| 5,215,089 A | 6/1993 | Baker, Jr. |
| 5,222,971 A | 6/1993 | Willard et al. |
| 5,224,491 A | 7/1993 | Mehra |
| 5,259,394 A | 11/1993 | Bens |
| 5,265,608 A | 11/1993 | Lee et al. |
| 5,282,468 A | 2/1994 | Klepinski |
| 5,295,959 A | 3/1994 | Gurbel et al. |
| 5,299,569 A | 4/1994 | Wernicke et al. |
| 5,304,206 A | 4/1994 | Baker, Jr. et al. |
| 5,314,453 A | 5/1994 | Jeutter |
| 5,318,592 A | 6/1994 | Schaldach |
| 5,324,310 A | 6/1994 | Greeninger et al. |
| 5,324,325 A | 6/1994 | Moaddeb |
| 5,330,507 A | 7/1994 | Schwartz |
| 5,330,515 A | 7/1994 | Rutecki et al. |
| 5,331,966 A | 7/1994 | Bennett et al. |
| 5,351,394 A | 10/1994 | Weinberg |
| 5,387,234 A | 2/1995 | Hirschberg |
| 5,408,744 A | 4/1995 | Gates |
| 5,411,540 A | 5/1995 | Edell et al. |
| 5,458,626 A | 10/1995 | Krause |
| 5,509,888 A | 4/1996 | Miller |
| 5,522,854 A | 6/1996 | Ideker et al. |
| 5,522,874 A | 6/1996 | Gates |
| 5,529,067 A | 6/1996 | Larsen et al. |
| 5,531,779 A | 7/1996 | Dahl et al. |
| 5,535,752 A | 7/1996 | Halperin et al. |
| 5,540,734 A | 7/1996 | Zabara |
| 5,540,735 A | 7/1996 | Wingrove |
| 5,545,132 A | 8/1996 | Fagan et al. |
| 5,545,202 A | 8/1996 | Dahl et al. |
| 5,571,150 A | 11/1996 | Wernicke et al. |
| 5,575,809 A | 11/1996 | Sasaki |
| 5,578,061 A | 11/1996 | Stroetmann et al. |
| 5,634,878 A | 6/1997 | Grundei et al. |
| 5,643,330 A | 7/1997 | Holsheimer et al. |
| 5,651,378 A | 7/1997 | Matheny et al. |
| 5,683,430 A | 11/1997 | Markowitz et al. |
| 5,690,681 A | 11/1997 | Geddes et al. |
| 5,692,882 A | 12/1997 | Bozeman, Jr. et al. |
| 5,695,468 A | 12/1997 | Lafontaine et al. |
| 5,700,282 A | 12/1997 | Zabara |
| 5,707,400 A | 1/1998 | Terry, Jr. et al. |
| 5,715,837 A | 2/1998 | Chen |
| 5,725,471 A | 3/1998 | Davey et al. |
| 5,725,563 A | 3/1998 | Klotz |
| 5,727,558 A | 3/1998 | Hakki et al. |
| 5,741,316 A | 4/1998 | Chen et al. |
| 5,766,236 A | 6/1998 | Detty et al. |
| 5,766,527 A | 6/1998 | Schildgen et al. |
| 5,776,178 A | 7/1998 | Pohndorf et al. |
| 5,800,464 A | 9/1998 | Kieval |
| 5,807,258 A | 9/1998 | Cimochowski et al. |
| 5,810,735 A | 9/1998 | Halperin et al. |
| 5,814,079 A | 9/1998 | Kieval |
| 5,824,021 A | 10/1998 | Rise |
| 5,853,652 A | 12/1998 | Schildgen et al. |
| 5,861,012 A | 1/1999 | Stroebel |
| 5,861,015 A | 1/1999 | Benja-Athon |
| 5,876,422 A | 3/1999 | van Groeningen |
| 5,891,181 A | 4/1999 | Zhu |
| 5,904,708 A | 5/1999 | Goedeke |
| 5,913,876 A | 6/1999 | Taylor et al. |
| 5,916,239 A | 6/1999 | Geddes et al. |
| 5,919,220 A | 7/1999 | Stieglitz et al. |
| 5,928,272 A | 7/1999 | Adkins et al. |
| 5,938,596 A | 8/1999 | Woloszki et al. |
| 5,967,986 A | 10/1999 | Cimochowski et al. |
| 5,967,989 A | 10/1999 | Cimochowski et al. |
| 5,987,352 A | 11/1999 | Klein et al. |
| 5,987,746 A | 11/1999 | Williams |
| 5,989,230 A | 11/1999 | Frassica |
| 5,991,667 A | 11/1999 | Feith |
| 6,006,134 A | 12/1999 | Hill et al. |
| 6,016,449 A | 1/2000 | Fischell et al. |
| 6,023,642 A | 2/2000 | Shealy et al. |
| 6,050,952 A | 4/2000 | Hakki et al. |
| 6,052,623 A | 4/2000 | Fenner et al. |
| 6,058,331 A | 5/2000 | King |
| 6,061,596 A | 5/2000 | Richmond et al. |
| 6,073,048 A | 6/2000 | Kieval et al. |
| 6,077,227 A | 6/2000 | Miesel et al. |
| 6,077,298 A | 6/2000 | Tu et al. |
| 6,106,477 A | 8/2000 | Miesel et al. |
| 6,110,098 A | 8/2000 | Renirie et al. |
| 6,161,029 A | 12/2000 | Spreigl et al. |
| 6,161,047 A | 12/2000 | King et al. |
| 6,178,349 B1 | 1/2001 | Kieval |
| 6,206,914 B1 | 3/2001 | Soykan |
| 6,208,894 B1 | 3/2001 | Schulman et al. |
| 6,231,516 B1 | 5/2001 | Keilman et al. |
| 6,253,110 B1 | 6/2001 | Brabec et al. |
| 6,255,296 B1 | 7/2001 | Daniels |
| 6,292,695 B1 | 9/2001 | Webster, Jr. et al. |
| 6,292,703 B1 | 9/2001 | Meier et al. |
| 6,393,324 B2 | 5/2002 | Gruzdowich et al. |
| 6,397,109 B1 | 5/2002 | Cammilli et al. |
| 6,401,129 B1 | 6/2002 | Lenander |
| 6,438,428 B1 | 8/2002 | Axelgaard et al. |
| 6,442,435 B2 | 8/2002 | King et al. |
| 6,512,949 B1 | 1/2003 | Combs et al. |
| 6,522,926 B1 | 2/2003 | Kieval et al. |
| 6,564,101 B1 | 5/2003 | Zikria |
| 6,600,956 B2 | 7/2003 | Maschino et al. |
| 6,616,624 B1 | 9/2003 | Kieval |
| 6,666,826 B2 | 12/2003 | Salo et al. |
| 6,701,186 B2 | 3/2004 | Spinelli et al. |

(56) References Cited

U.S. PATENT DOCUMENTS

| | | |
|---|---|---|
| 6,704,598 B2 | 3/2004 | Ding et al. |
| 6,748,272 B2 | 6/2004 | Carlson et al. |
| 6,766,189 B2 | 7/2004 | Yu et al. |
| 6,768,923 B2 | 7/2004 | Ding et al. |
| 6,779,257 B2 | 8/2004 | Kiepen et al. |
| 6,850,801 B2 | 2/2005 | Kieval et al. |
| 6,894,204 B2 | 5/2005 | Dunshee et al. |
| 6,942,686 B1 | 9/2005 | Barbut et al. |
| 6,985,774 B2 | 1/2006 | Kieval et al. |
| 7,155,284 B1 | 12/2006 | Whitehurst et al. |
| 7,158,832 B2 | 1/2007 | Kieval et al. |
| 2001/0020177 A1 | 9/2001 | Gruzdowich et al. |
| 2001/0023367 A1 | 9/2001 | King et al. |
| 2002/0005982 A1 | 1/2002 | Borlinghaus |
| 2002/0103516 A1 | 8/2002 | Patwardhan et al. |
| 2002/0128700 A1 | 9/2002 | Cross, Jr. |
| 2002/0151051 A1 | 10/2002 | Li |
| 2003/0040785 A1 | 2/2003 | Maschino et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2004/0010303 A1 | 1/2004 | Bolea et al. |
| 2004/0019364 A1 | 1/2004 | Kieval et al. |
| 2004/0062852 A1 | 4/2004 | Schroeder et al. |
| 2004/0102818 A1 | 5/2004 | Hakky et al. |
| 2004/0193231 A1 | 9/2004 | David et al. |
| 2004/0220645 A1 | 11/2004 | Freed et al. |
| 2004/0249416 A1 | 12/2004 | Yun et al. |
| 2004/0249417 A1 | 12/2004 | Ransbury et al. |
| 2004/0254616 A1 | 12/2004 | Rossing et al. |
| 2005/0021092 A1 | 1/2005 | Yun et al. |
| 2005/0043675 A1 | 2/2005 | Pastore et al. |
| 2005/0143779 A1 | 6/2005 | Libbus |
| 2005/0143785 A1 | 6/2005 | Libbus |
| 2005/0149126 A1 | 7/2005 | Libbus |
| 2005/0149127 A1 | 7/2005 | Libbus |
| 2005/0149128 A1 | 7/2005 | Heil et al. |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149155 A1 | 7/2005 | Scheiner et al. |
| 2005/0149156 A1 | 7/2005 | Libbus et al. |
| 2005/0182468 A1 | 8/2005 | Hunter et al. |
| 2005/0251212 A1 | 11/2005 | Kieval et al. |
| 2005/0261741 A1 | 11/2005 | Libbus et al. |
| 2006/0004417 A1 | 1/2006 | Rossing et al. |
| 2006/0074453 A1 | 4/2006 | Kieval et al. |
| 2006/0135998 A1* | 6/2006 | Libbus et al. ............ 607/2 |
| 2006/0224222 A1 | 10/2006 | Bradley et al. |
| 2006/0293712 A1 | 12/2006 | Kieval et al. |
| 2007/0049989 A1 | 3/2007 | Rossing et al. |
| 2007/0156201 A1 | 7/2007 | Rossing et al. |
| 2008/0167694 A1 | 7/2008 | Bolea et al. |
| 2008/0167696 A1 | 7/2008 | Cates et al. |
| 2008/0171923 A1 | 7/2008 | Bolea et al. |
| 2008/0172101 A1 | 7/2008 | Bolea et al. |
| 2008/0177339 A1 | 7/2008 | Bolea et al. |
| 2008/0177348 A1 | 7/2008 | Bolea et al. |
| 2008/0177364 A1 | 7/2008 | Bolea et al. |
| 2008/0177365 A1 | 7/2008 | Bolea et al. |
| 2008/0177366 A1 | 7/2008 | Bolea et al. |

FOREIGN PATENT DOCUMENTS

| | | |
|---|---|---|
| WO | WO 99/26530 | 6/1999 |
| WO | WO 99/42039 | 8/1999 |
| WO | WO 99/42176 | 8/1999 |
| WO | WO 99/51286 A1 | 10/1999 |
| WO | WO 00/16686 | 3/2000 |
| WO | WO 01/00273 | 1/2001 |
| WO | WO 02/26314 | 4/2002 |
| WO | WO 02/070039 | 9/2002 |
| WO | WO 03/076008 | 9/2003 |
| WO | WO 2006/031331 A1 | 3/2006 |

OTHER PUBLICATIONS

Bilgutay et al., "Surgical Treatment of Hypertension with Reference to Baropacing," *Am. J of Cardiology*, vol. 17, (May 1966), pp. 663-667.

Bock et al, "Fine Structure of Baroreceptor Terminals in the Carotid Sinus of Guinea Pigs and Mice," *Cell & Tissue Research*, vol. 170, (1976), pp. 95-112.

Brattstrom, "Influence of Continuous and Intermittent (R-Wave Triggered) Electrical Stimulation of the Carotid Sinus Nerve on the Static Characteristic of the Circularoty Regulator," *Experientia*, vol. 28, (1972), pp. 414-416.

Coleridge et al., "Impulse in Slowly Conducting Vagal Fibers from Afferent Endings in the Veins, Atria, and Arteries of Dogs and Cats," *Circ. Res.*, vol. 33, (Jul. 1973), pp. 87-97.

Coleridge et al., "Reflex Effects of Stimulating Baroreceptors in the Pulmonary Artery," *J. Physciol.* (1963) 166:197-210.

Correspondence, *The New England of Journal of Medicine*, vol. 281, No. 2., (Jul. 3, 1969), p. 103.

Ebert et al., "Fentanyl-diazepam Anesthesia with or without N2O does not Attenuate Cardiopulmonary Baroreflex-Mediated Vasoconstrictor Responses to Controlled Hypovolemia in Humans," *Anesth Analg* (1988) 67(6): 548-554.

Eckberg et al., "Baroreflex anatomy" In: Monographs of the Physiological Society (43): *Human Baroreflex in Health and Disease*. Oxford, UK: Clarendon Press, (1992), pp. 19-30.

Goldberger et al., "New Technique for Vagal Nerve Stimulation," *Journal of Neuroscience Methods*, vol. 91, (1999), pp. 109-114.

Hainsworth, "Cardiovascular Reflexes From Ventricular & Coronary Receptors," *Adv. Exp. Med. Biol.*, vol. 381, (1999), pp. 157-174.

Harrison, "Carotid Sinus Stimulation for the Treatment of Angina Pectoris," *Official Journal of the Calif. Medical Assoc.*, vol. 112, No. 3, (Mar. 1970), pp. 78-79.

Itoh, "Studies on the Carotid Body & the Carotid Sinus Effects on the Heart by Electrical Stimulation of the Carotid Sinus Wall," *Jap. Heart J.*, vol. 13, No. 2, (Mar. 1972), pp. 136-149.

Kostreva et al., "Hepatic Vein, Hapatic Parenchymal, and Inferior Vena Caval Mechanoreceptors with Phrenic Afferents," *Am. J. Physiol.*, vol. 265, 1993, pp. G15-G20.

Krauhs, "Structure of Rat Aortic Baroreceptors & Their Relationship to Connective Tissue," *Journal of Neurocytology*, vol. 8, (1979), pp. 401-414.

Lindblad et al., "Circulatory Effects of Carotid Sinus Stimulation & Changes in Blood Volume Distribution in Hypertensive Man", *Acta. Physiol. Scand.*, vol. 111, (Mar. 1981), pp. 299-306.

Mifflin et al., "Rapid Resetting of Low Pressure Vagal Receptors in the Superior Vena Cava of the Rat," *Circ. Res*, vol. 51,(1982) pp. 241-249.

Neufeld, "Stimulation of the Carotid Baroreceptors Using a Radio-Frequency Method," *Israel J. Med. Sci.*, vol. 1, No. 4, (Jul. 1965), pp. 630-632.

Peters et al., "Cardiovascular response to time delays of electrocardiogram-coupled electrical stimulation of carotid sinus nerves in dogs," *Journal of the Autonomic Nervous Systems*, vol. 25, (1988), pp. 173-180.

Peters et al., "The Principle of Electrical Carotid Sinus Nerve Stimulation: A Nerve Pacemaker System for Angina Pectoris and Hypertension Therapy," *Annals of Biomedical Engineering*, vol. 8 .(1980), pp. 445-458.

Rau et al., "Psycholphysiology of Arterial Baroreceptors and the Etiology of Hypertension," *Biol. Psychol.*, vol. 57, (2001), pp. 179-201.

Reich, "Implantation of a Carotid Sinus Nerve Stimulator," *AORN Journal*, (Dec. 1969.), pp. 53-56.

Richter et al., "The Course of Inhibition of Sympathetic Activity during Various Patterns of Carotid Sinus Nerve Stimulation," *Pflugers Arch.*, vol. 317, (1970), pp. 110-123.

(56) References Cited

OTHER PUBLICATIONS

Schauerte et al., "Transvenous parasympathetic nerve stimulation in the inferior vena cava and atrioventricular conduction," *J. Cardiovasc. Electrophysiol.*, (Jan. 2000), 1 page.

Sedin, "Responses of the Cardiovascular System to Carotid Sinus Nerve Stimulation," *Upsala J Med Sci*, Vo. 81, (1976), pp. 1-17.

Silber, "The Treatment of Heart Disease," *Heart Disease*, 2.sup.nd Edition, MacMillan Publishing Co., (1987), p. 1642.

Solti, "Baropacing of the Carotid Sinus Nerve for Treatment of Intractable Hypertension," *Zeitschrift Fur Kardiologie*, band 64, Heft 4, (1975), pp. 368-374.

Solti, "The Haemodynamic Basis of Anginal Relief Produced by Stimulation of the Carotid Sinus Nerve," *Acta Medica Academiae Scientiarum Hungaricae*, vol. 30 (1-2), (1973), pp. 61-65.

Stefanadis et al. "Non-invasive heat delivery to arterial stented segments in vivo: Effect of heat on neointimal hyperplasia (Abstr)" *J Am Coll Cardiol*, #1041-89, (Feb. 2000), p. 14A.

Tarver et al, "Clinical Experience with a Helical Bipolar Stimulating Lead," *PACE*, vol. 15, Part II, (Oct. 1992), pp. 1545-1556.

Tsakiris, "Changes in Left Ventricular End Diastolic Volume Pressure Relationship After Acute Cardiac Denervation," Abstracts of the 40th sup. Scientific Sessions, Supplement II to *Circulation*, vols. XXXV & XXXVI, (Oct. 1967), II-253, 1 sheet.

Warzel et. al., Effects of Carotis Sinus Nerve Stimulation at Different Times in the Respiratory and Cardiac Cycles on Variability of Heart Rate and Blood Pressure of Normotensive and Renal Hypertensive Dogs, *Journal of the Autonomic Nervous System*, (1989) 26:121-127.

Warzel et. al., "The Effect of Time of Electrical Stimulation of the Carotid Sinus on the Amount of Reduction in Arterial Pressure," *Pflugers Arch.*, (1972) 337:39-44.

Yatteau, "Laryngospasm Induced by a Carotid-Sinus-Nerve Stimulator", *N Engl J Med.*, (1971) 284(13): 709-710.

U.S. Appl. No. 10/284,063, filed Oct. 29, 2002; first named inventor: Robert Kieval.

U.S. Appl. No. 60/883,721, filed Feb. 27, 2007; first named inventor: Robert Kieval.

U.S. Appl. No. 60/894,957, filed Mar. 15, 2007; first named inventor: Thomas Crowley.

International Search Report and Written Opinion of PCT Application No. PCT/US2008/070770, mailed Nov. 7, 2008, 9 pages total.

Extended European Search Report (EP08 78 2199), dated Jan. 19, 2011.

European Patent Application No. 08782119.7 Office Action; Apr. 11, 2012. Four pages.

International Preliminary Report on Patentability, dated Feb. 4, 2010.

\* cited by examiner

BAROREFLEX ACTIVATION THERAPY WITH INCREMENTALLY CHANGING INTENSITY

CROSS-REFERENCES TO RELATED APPLICATIONS

This application claims the benefit of provisional application No. 60/951,660 filed on Jul. 24, 2007, the full disclosure of which is incorporated herein by reference.

This application is related to, but does not claim the benefit of the following U.S. patents and applications, all of which are is fully incorporated herein by reference in their entirety: U.S. Pat. Nos. 6,522,926; 6,616,624; 6,985,774; 7,158,832; 6,850,801; PCT Patent Application No. PCT/US01/30249, filed Sep. 27, 2001 U.S. patent application Ser. Nos. 10/284, 063 filed Oct. 29, 2002; 10/453,678 filed Jun. 2, 2003; 10/402, 911 filed Mar. 27, 2003; 10/402,393 filed Mar. 27, 2003; 60/549,760 filed Mar. 2, 2004; 10/818,738 filed Apr. 5, 2004; and 60/584,730 filed Jun. 30, 2004; 10/958,694 filed Oct. 4, 2004; 11/071,602 filed Mar. 2, 2005; 11/168,231 filed Jun. 27, 2005; and 60/88,2478 filed Dec. 28, 2006; and 60/883,721 filed Jan. 5, 2007; and 60/894,957 filed Mar. 15, 2007; the full disclosure of all of which is hereby incorporated by reference.

BACKGROUND OF THE INVENTION

The present invention relates generally to medical devices and methods of use for the treatment and/or management of cardiovascular, neurological, and renal disorders, and more specifically to devices and methods for controlling the baroreflex system of a patient for the treatment and/or management of cardiovascular, neurological, and renal disorders and their underlying causes and conditions, more particularly to baroreflex systems and methods that allow a physician to program the device for providing a predetermined response to changes in the patient's condition.

Hypertension, or high blood pressure, is a major cardiovascular disorder that is estimated to affect 65 million people in the United States alone, and is a leading cause of heart failure and stroke. It is listed as a primary or contributing cause of death in over 200,000 patients per year in the United States alone. Hypertension occurs in part when the body's smaller blood vessels (arterioles) constrict, causing an increase in blood pressure. Because the blood vessels constrict, the heart must work harder to maintain blood flow at the higher pressures. Sustained hypertension may eventually result in damage to multiple body organs, including the kidneys, brain, eyes, and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke.

Sustained high blood pressure may eventually result in an enlarged and damaged heart (hypertrophy), which may lead to heart failure. Heart failure is the final common expression of a variety of cardiovascular disorders, including ischemic heart disease. It is characterized by an inability of the heart to pump enough blood to meet the body's needs and results in fatigue, reduced exercise capacity and poor survival. Congestive heart failure (CHF) is an imbalance in pump function in which the heart fails to maintain the circulation of blood adequately. The most severe manifestation of CHF, pulmonary edema, develops when this imbalance causes an increase in lung fluid due to leakage from pulmonary capillaries into the lung. The most common cause of heart failure is coronary artery disease, which is secondary to loss of left ventricular muscle, ongoing ischemia, or decreased diastolic ventricular compliance. Other causes of CHF include hypertension, valvular heart disease, congenital heart disease, other cardiomyopathies, myocarditis, and infectious endocarditis.

One preferred heart failure treatment method is to use cardiac rhythm management devices ("cardiac rhythm management device") such as cardiac resynchronization therapies ("CRT") using pacemakers and combination pace makers/defibrillators ("ICD"). Another CHF treatment method that has been proposed is to affect the baroreflex system to help the heart perform more efficiently by way of controlling the patient's blood pressure. Baroreflex activation may generally decrease neurohormonal activation, thus decreasing cardiac afterload, heart rate, sympathetic drive to the heart and the like. By decreasing the demands placed on the heart, baroreflex activation may help prevent or treat CHF.

A number of different treatment modalities may be attempted for treating heart failure, such as medications, mechanical restriction of the heart, surgical procedures to reduce the size of an expanded heart and the like. These include vasodilators to reduce the blood pressure and ease the workload of the heart, diuretics to reduce fluid overload, inhibitors and blocking agents of the body's neurohormonal responses, and other medicaments. Various surgical procedures have also been proposed for these maladies. For example, heart transplantation has been proposed for patients who suffer from severe, refractory heart failure. Alternatively, an implantable medical device such as a ventricular assist device (VAD) may be implanted in the chest to increase the pumping action of the heart. Alternatively, an intra-aortic balloon pump (IABP) may be used for maintaining heart function for short periods of time, but typically no longer than one month.

Of course, no "perfect" treatment method for heart failure has yet been developed. Although some of the therapies mentioned above may be highly effective in some cases, some may have unwanted side effects or provide little benefit to some patients. Because CHF is such a pervasive health problem, with high morbidity, mortality and costs to society, improved treatment methods are continually sought. Additionally, with the use of any of such devices, the physiological conditions of a patient may change rapidly in response to internal and/or external conditions such that course of therapy may need to readjust to provide optimum performance to the patient.

Therefore, it would be desirable to provide improved methods and apparatus having smart processes for controlling their operation. Ideally, such methods and apparatus would be minimally invasive, with few if any significant side effects. Ideally, one or more underlying mechanisms causing heart failure could be treated in some cases. At least some of these objectives will be met by the present invention.

BRIEF SUMMARY OF THE INVENTION

To address the problems of hypertension, heart failure, other cardiovascular disorders, nervous system and renal disorders, the present invention provides methods, and devices (i.e., baroreflex activation device) for practicing the same, by which at least one baroreflex system within a patient's body is activated to achieve effects that include reducing excessive blood pressure, autonomic nervous system activity, and neurohormonal activation. Such activation systems suggest to the brain an increase in blood pressure, and the brain in turn regulates (e.g., decreases) the level of sympathetic nervous system and neurohormonal activation, and increases parasympathetic nervous system activation, thus reducing blood pressure and having a beneficial effect on the cardiovascular system and other body systems.

The methods and devices according to the present invention may be used to activate baroreceptors, mechanoreceptors, pressoreceptors, or any other venous heart, or cardiopulmonary receptors which affect the blood pressure, nervous system activity, and neurohormonal activity in a manner analogous to baroreceptors in the arterial vasculation. For convenience, all such venous receptors (and/or nerves carrying signals from such receptors) will be referred to collectively herein as "baroreceptors."

The present invention provides systems, devices, and methods for using the same. The methods, devices, and systems embodying features of the present invention, allow for activating (stimulating) the baroreflex system of a patient using a baroreflex activation device which senses/monitors/interprets the sensed data associated with a parameter indicative of a physiological condition of a patient and which adjusts the course of therapy according to magnitude of change and/or rate of change of the parameter. By way of example, the system may increase or decrease the intensity of the therapy depending on whether the magnitude of a given parameter has changed over a course of time, and if so, whether such change was an increase or decrease.

It should be further understood by those skilled in the art that the methods, devices, and systems according to the present invention are further applicable to modifying any one or more of the nervous system activity of the patient, autonomic nervous system activity of the patient, sympathetic/parasympathetic nervous system activity of the patient, or metabolic activity of the patient.

In some embodiments, the present invention provides for the activation of the baroreflex system of a patient with a baroreflex activation device. A therapy for a patient is normally determined and chosen by the healthcare provider. One or more parameters which are indicative of one or more physiological conditions of the patient are chosen and a target value for such parameter is selected. By way of example, and not limitation, the parameter may be the CO2 level in the blood of the patient which is indicative of the blood pressure. Other examples of such parameters include, but are not limited to: heart rate, blood pressure, ECG, oxygen saturation, blood pH, activity level (e.g., exercising, rest), prone posture, supine posture, core body temperature, respiration rate, and respiration depth. In some embodiments, an initial target range (as used herein, a target range may be a baseline or a range from a baseline or lower limit to an upper limit, unless otherwise stated) number to another for the one or more parameters are set and their values are sensed by one or more sensors. The parameter may be sensed such that the system becomes aware of the value or condition of the parameter. In some embodiments, the parameter is sensed/monitored during a time period determined by the healthcare provider. The methods, embodying features of the present invention, modify/adjust the baroreflex activation therapy in response to a class that a present change in the value and/or a rate of change of the monitored parameter is a member of. As used herein, the terms sensed/sensing and monitor/monitoring may be used interchangeably unless otherwise stated.

In some embodiments, the baroreflex activation therapy comprises one or more therapy regimens, with the regimens delivering the baroreflex activation therapy at different doses/intensities such that the baroreflex system is activated (stimulated) to varying degrees. In some embodiments, changing the dose/intensity of a regimen includes changing one or more characteristics of pulses generated by a pulse generator for activating the baroreflex activation device. Such characteristics include one or more of duty cycle, pulse amplitude, pulse width, pulse frequency, pulse separation, pulse waveform, pulse polarity, pulse shape, and pulse phase. In some embodiments, the baroreflex activation therapy is delivered in incremental doses, either in an increasing manner or decreasing manner in order to effectively "ramp up" or "ramp down" therapy. Providing therapy in incremental dosages allows for monitoring of patient response to the therapy and customizing the therapy for each patient. In some embodiments, baroreflex activation therapy regimens are delivered at different doses/intensities such that the baroreflex system of the patient does not over-respond to a change in therapy, for example by causing a blood pressure surge in the patient when the therapy is paused or deactivated.

In some embodiments, the one or more parameters are sensed by one or more sensors. The parameter may be sensed such that the system becomes aware of the value or condition of the parameter. In some embodiments, the parameter is sensed/monitored during a time period determined by the healthcare provider. The methods, embodying features of the present invention, modify/adjust the baroreflex activation therapy in response to classes of changes (as used herein, unless otherwise stated classes are not limited to a specific number and may range depending on the particular usage or application or therapy) in the monitored parameter. In some embodiments, the therapy is delivered at an initial dose/intensity. Upon sensing a change in the parameter, the method compares a change in the value of the sensed parameter one or more predetermined classes. In some useful embodiments, a predetermined intensity step-size is associated with each of the one or more predetermined classes.

In some embodiments, the value of the sensed/monitored parameters is compared to the target value of that parameter and based on the results of the comparison, it is determined whether the value (magnitude) of the parameter has changed and if so, whether it has increased or decreased. The intensity of the baroreflex activation therapy will vary during the course of therapy depending on the class that this change in the parameter's magnitude is a member of.

In some embodiments, the change in magnitude is relatively large and the corresponding change in the baroreflex activation therapy intensity is relatively large. In some embodiments, the change in magnitude is relatively small and the corresponding change in the baroreflex activation therapy intensity is relatively small.

In some embodiments, methods embodying features of the present invention include activating a baroreflex system of the patient with a baroreflex activation device according to a baroreflex activation therapy and establishing an initial target range for a parameter indicative of the physiological condition. The physiological parameter is monitored and the intensity of the baroreflex activation therapy as modified in response to a class of change that a present change in the value of the monitored parameter is a member of. For example, if an increase in the magnitude of the monitored physiological parameter is determined to be a member of a class of large changes, then the baroreflex activation therapy intensity may be increased by a predetermined large step-sized associated with large changes in the monitored physiologic parameter.

If the increase in the magnitude of the monitored physiological parameter is determined to be a member of a class of small changes, however, the baroreflex activation therapy intensity may be increased by a predetermined small step-sized associated with small changes in the monitored physiologic parameter. By way of a second example, if a decrease in the magnitude of the monitored physiological parameter is determined to be a member of a class of large changes, then the baroreflex activation therapy intensity may be decreased by a predetermined large step-sized associated with large changes in the monitored physiologic parameter. If the decrease in the magnitude of the monitored physiological parameter is determined to be a member of a class of small changes, however, the baroreflex activation therapy intensity may be decreased by a predetermined small step-sized associated with small changes in the monitored physiologic parameter.

In some embodiments the physiological parameter is monitored over time and changes in its magnitude are identified. In some embodiments, the various changes for the physiological parameter are classified into a prescribed classification system. The changes may be classified; by way of example, as large changes or small changes. In some embodiments, a pre-determined series of step-sizes for either increasing or decreasing intensity is established. In some useful embodiments, each of these intensity step-sizes are associated with a particular class of physiological parameter change. The size of these intensity step-sizes may be determined through experimentation and/or the healthcare provider/patient and/or the baroreflex activation therapy system learning through historical data in its memory/processor and new information becoming available to it. In some embodiments, as a change in the parameter is detected, based on its classification, a particular baroreflex activation therapy intensity step-size is applied.

In some embodiments, methods embodying features of the present invention include establishing a prescribed baroreflex activation therapy intensity step size associated with a patient parameter having a first rate of change. The method further includes establishing a prescribed baroreflex activation therapy intensity step size associated with the patient parameter having a second change rate. An initial baroreflex activation therapy intensity is established and an initial target range is established for the patient parameter. Baroreflex activation therapy is delivered to the patient while the patient parameter is monitored.

In some embodiments, it is then determined whether the value of the parameter is changing and if so in what direction. If the there is no change, the baroreflex activation therapy continues as before and the parameter continues to be monitored. If the magnitude of the parameter is increasing, it is then determined what class the rate is considered to be. For example, the rate of change may be a member of a class of large rates or a member of a class of small rates. If the rate of change is large rate of change, the baroreflex activation therapy intensity is increased by a step-size prescribed for this category. If the rate of change is a small rate of change, the baroreflex activation therapy intensity is increased by a step-size prescribed for this category (e.g., a relatively small step-size). In some embodiments, once the baroreflex activation therapy intensity has been readjusted the baroreflex activation therapy continues with the patient parameter being monitored.

In an embodiment, a system for treating a patient, embodying features of the present invention includes a baroreflex activation device for activating a baroreflex of a patient according to a baroreflex activation therapy. In some embodiments, the baroreflex activation therapy includes a plurality of dose/intensity regimens. By way of example, the system further includes a therapy circuitry for generating the therapy as well as a controller which is connectable to the therapy circuitry, and which is configured for providing the signal and the corresponding instructions for generating the activation pulses. The device also includes a memory system in communication with the controller and which is configured for storing information regarding the baroreflex activation therapy.

In some embodiments, the therapy circuitry includes a pulse generator which is configured for generating stimulation pulses, having different dose/intensity levels to activate the baroreflex system of the patient to various degrees. In some embodiments, the therapy includes a plurality of regimens wherein at least one of which is different than another regimen.

The systems, embodying features of the present invention, may further include at least one electrode assembly which is locatable proximate one or more baroreceptors of the patient. The system, in some embodiments, includes at least one monitoring system which is connectable to the controller and is configured for monitoring of a patient's parameter. The system, in some embodiments, further includes at least one sensing system which is connectable to the controller and is configured for sensing of the parameter. The controller is configured to adjust/modify the therapy based on information received from the sensed data. The therapy is then delivered to the patient by way of the one or more electrode assemblies.

In an embodiment, the system further includes a switching circuitry which is connectable to the monitoring circuitry and the therapy circuitry for routing the necessary information to and from various components and other circuitries, and thereafter delivering the therapy to the patient by way of the at least one electrode assembly.

Generally, any of a number of suitable anatomical structures may be activated to provide baroreflex activation. For example, in various embodiments, activating the baroreflex system may involve activating one or more baroreceptors, one or more nerves coupled with a baroreceptor, a carotid sinus nerve, or some combination thereof. In embodiments where one or more baroreceptors are activated, the baroreceptor(s) may sometimes be located in arterial vasculature, such as but not limited to a carotid sinus, aortic arch, heart, common carotid artery, subclavian artery, pulmonary artery, femoral artery and/or brachiocephalic artery. Alternatively, a baroreflex activation device may be positioned in the low-pressure side of the heart or vasculature, as described in U.S. patent application Ser. No. 10/284,063, previously incorporated by reference, in locations such as an inferior vena cava, superior vena cava, portal vein, jugular vein, subclavian vein, iliac vein, azygous vein, pulmonary vein and/or femoral vein. The baroreflex activation may be achieved, in various embodiments, by electrical activation, mechanical activation, thermal activation and/or chemical activation. Furthermore, baroreflex activation may be continuous, pulsed, periodic or some combination thereof in various embodiments.

The baroreflex activation device may comprise any of a wide variety of devices that utilize mechanical, electrical, thermal, chemical, biological or other means to activate the baroreflex, although in describing the present invention electrical activation will be used. The baroreflex may be activated directly or indirectly via adjacent vascular tissue. In some embodiments, systems embodying features of the present invention, the baroreflex activation device is implantable within the patient, such as within the patient's venous or arterial vasculature. For example, the device may be implantable within venous or arterial vasculature. In various embodiments, the baroreflex activation device may be positioned inside a vascular lumen (i.e., intravascularly), outside a vascular wall (i.e., extravascularly) or within a vascular wall (i.e., intramurally). To maximize therapeutic efficacy, a mapping method may be employed to precisely locate or position the baroreflex activation device. For embodiments utilizing electrical means to activate the baroreflex, various electrode designs are provided. The electrode designs may be particularly suitable for connection to the carotid arteries at or near the carotid sinus, and may be designed to minimize extraneous tissue stimulation.

In some embodiments, sensing of the parameter is achieved by way of one or more suitable physiological sensors. The sensors may be external or internally locatable within the patient's body. In some embodiments, the sensor comprising one or more of extracardiac electrocardiogram, intracardiac electrocardiogram, pressure sensor, and accelerometer. Furthermore, the sensor may be adapted to sense any suitable characteristics, condition, change or the like. Furthermore, the sensor may be adapted to sense any of a number of different patient parameters, such as but not limited to an intracardiac pressure, a heart rate and a timing of contractions of atria and ventricles of the heart.

In some embodiments, the sensor is configured to sense one or more parameters of the battery of the baroreflex activation device. The sensor may determine that the battery power source is approaching a time for replacement. For example, a device may be programmed to sense when the battery has sufficient charge to operate the device effectively (as it is currently programmed) for another 60 days.

In some embodiments, a system for treating the patient includes at least one baroreflex activation device, at least one sensor coupled with the baroreflex activation device, and a processor coupled with the at least one baroreflex activation device and the at least one sensor for processing sensed data received from the sensor and for activating and/or modifying activation of baroreflex activation device and/or providing the appropriate baroreflex activation therapy.

In various embodiments, a control system may be used to generate a control signal which activates, deactivates or otherwise modulates the baroreflex activation device. The control system may operate in an open-loop or a closed-loop mode. For example, in the open-loop mode, the patient and/or physician may directly or remotely interface with the control system to prescribe the control signal. In the closed-loop mode, the control signal may be responsive to feedback from a sensor, wherein the response is dictated by a preset or programmable algorithm defining a stimulus/activation therapy and the plurality of regimen. The stimulus (activation) therapy is preferably selected to promote long term efficacy and to minimize power requirements. It is theorized that uninterrupted baroreflex activation may result in the baroreflex and/or central nervous system becoming less responsive over time, thereby diminishing the effectiveness of the therapy. Therefore, the stimulus therapy may be selected to modulate the baroreflex activation device in such a way that the baroreflex maintains its responsiveness over time. Specific examples of stimulus regimens which promote long term efficacy are described in the applications earlier above incorporated herein by reference in their entirety.

In one embodiment, the control system may be used to generate a control signal which adjusts baroreflex activation therapy based on sensed information. In one embodiment, baroreflex activation therapy is adjusted based on sensed information, such as battery depletion or another parameter indicative of the need to reduce therapy and such adjustment in therapy is performed in order to effectively "wean" a patient off of the therapy so as to prevent transient overshoot of blood pressure when therapy is paused, turned off or deactivated. The therapy adjustment is performed specific to the patient and can be based on a determination of how the patient will response to pausing, turning off or deactivating the therapy.

As suggested above, various embodiments of the inventive devices may be entirely intravascular, entirely extravascular, or partially intravascular and partially extravascular. Furthermore, devices may reside wholly in or on arterial vasculature, wholly in or on venous vasculature, or in or on some combination of both. In some embodiments, for example, implantable devices may be positioned within an artery or vein, while in other embodiments devices may be placed extravascularly, on the outside of an artery or vein. In yet other embodiments, one or more components of a device, such as electrodes, a controller or both, may be positioned outside the patient's body. In introducing and placing devices of the present invention, any suitable technique and access route may be employed. For example, in some embodiments an open surgical procedure may be used to place an implantable device. Alternatively, an implantable device may be placed within an artery or vein via a transvascular, intravenous approach. In still other embodiments, an implantable device may be introduced into vasculature via minimally invasive means, advanced to a treatment position through the vasculature, and then advanced outside the vasculature for placement on the outside of an artery or vein. For example, an implantable device may be introduced into and advanced through the venous vasculature, made to exit the wall of a vein, and placed at an extravascular site on an artery.

These and other aspects and embodiments of the present invention are described in further detail below, with reference to the attached drawings.

DETAILED DESCRIPTION OF THE INVENTION

Figure 1:
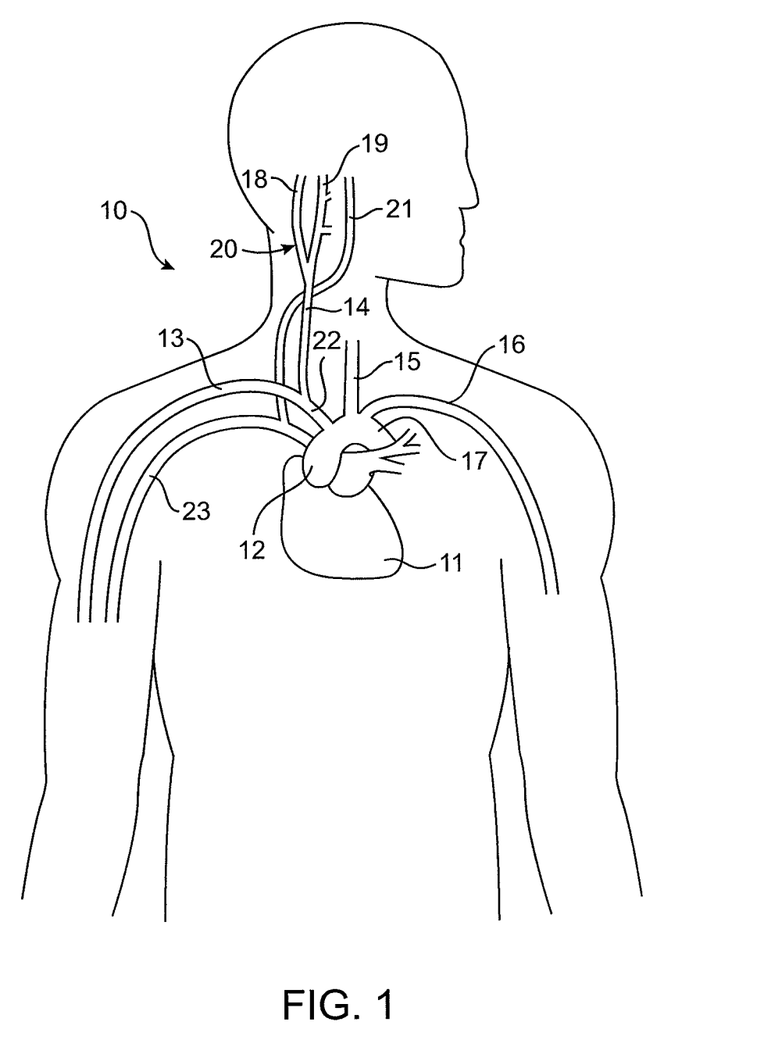
FIG. 1 is a schematic illustration of the upper torso of a human body showing the major arteries and veins and associated anatomy.
Figures 2A, 2B:
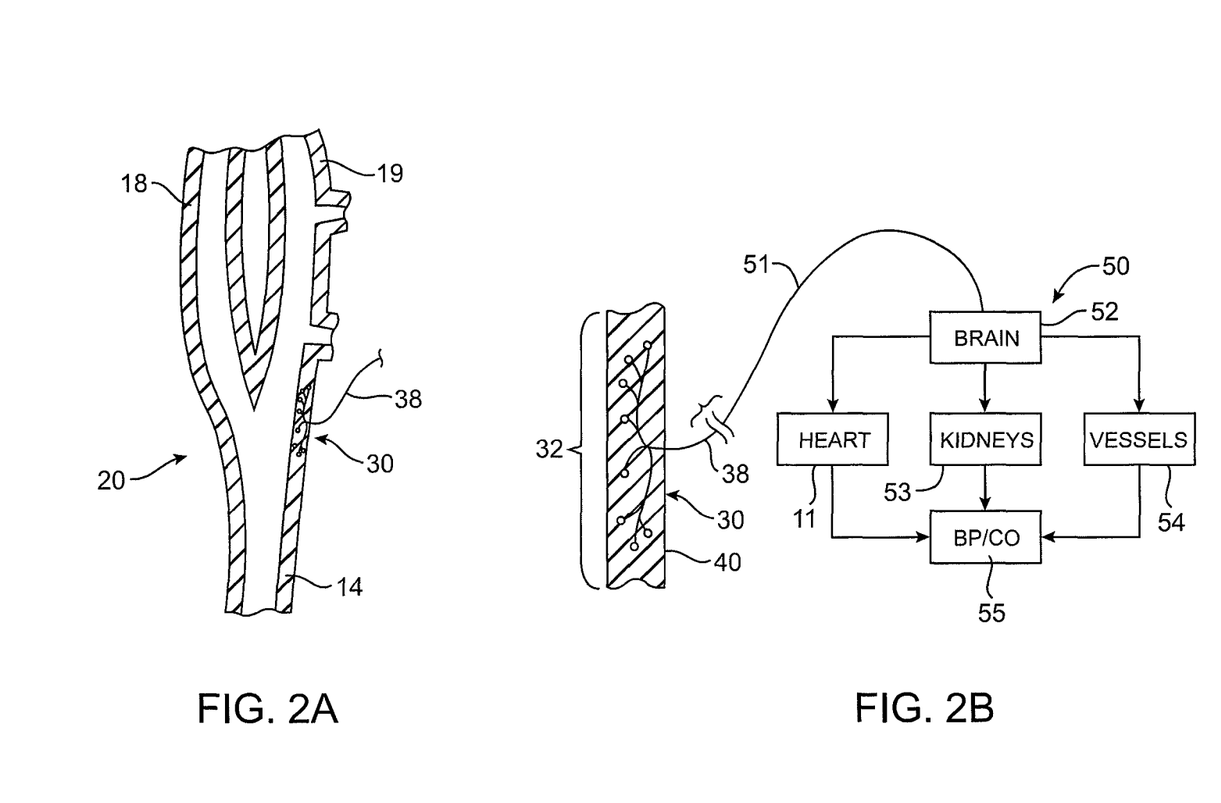
FIG. 2A is a cross sectional schematic illustration of a carotid sinus and baroreceptors within a vascular wall.
FIG. 2B is a schematic illustration of baroreceptors within a vascular wall and the baroreflex system.

Referring now to FIGS. 1, 2A and 2B, within the arterial walls of the aortic arch 12, common carotid arteries 14/15 (near the right carotid sinus 20 and left carotid sinus), subclavian arteries 13/16 and brachiocephalic artery 22 there are baroreceptors 30. For example, as best seen in FIG. 2A, baroreceptors 30 reside within the vascular walls of the carotid sinus 20. Baroreceptors 30 are a type of stretch receptor used by the body to sense blood pressure. An increase in blood pressure causes the arterial wall to stretch, and a decrease in blood pressure causes the arterial wall to return to its original size. Such a cycle is repeated with each beat of the heart. Baroreceptors 30 located in the right carotid sinus 20, the left carotid sinus and the aortic arch 12 play the most significant role in sensing blood pressure that affects baroreflex system 50, which is described in more detail with reference to FIG. 2B.

With reference now to FIG. 2B, a schematic illustration shows baroreceptors 30 disposed in a generic vascular wall 40 and a schematic flow chart of baroreflex system 50. Baroreceptors 30 are profusely distributed within the arterial walls 40 of the major arteries discussed previously, and generally form an arbor 32. The baroreceptor arbor 32 comprises a plurality of baroreceptors 30, each of which transmits baroreceptor signals to the brain 52 via nerve 38. Baroreceptors 30 are so profusely distributed and arborized within the vascular wall 40 that discrete baroreceptor arbors 32 are not readily discernable. To this end, baroreceptors 30 shown in FIG. 2B are primarily schematic for purposes of illustration.

In addition to baroreceptors, other nervous system tissues are capable of inducing baroreflex activation. For example, baroreflex activation may be achieved in various embodiments by activating one or more baroreceptors, one or more nerves coupled with one or more baroreceptors, a carotid sinus nerve or some combination thereof. Therefore, the phrase "baroreflex activation" generally refers to activation of the baroreflex system by any means, and is not limited to directly activating baroreceptor(s). Although the following description often focuses on baroreflex activation/stimulation and induction of baroreceptor signals, various embodiments of the present invention may alternatively achieve baroreflex activation by activating any other suitable tissue or structure.

Baroreflex signals are used to activate a number of body systems which collectively may be referred to as baroreflex system 50. Baroreceptors 30 are connected to the brain 52 via the nervous system 51, which then activates a number of body systems, including the heart 11, kidneys 53, vessels 54, and other organs/tissues via neurohormonal activity. Although such activation of baroreflex system 50 has been the subject of other patent applications by the inventors of the present invention, the focus of the present invention is a baroreflex system and methods using the same which allow for automatic shut off in certain conditions to prevent or minimized adverse effects the effect of baroreflex activation on the brain 52.

Figure 3:
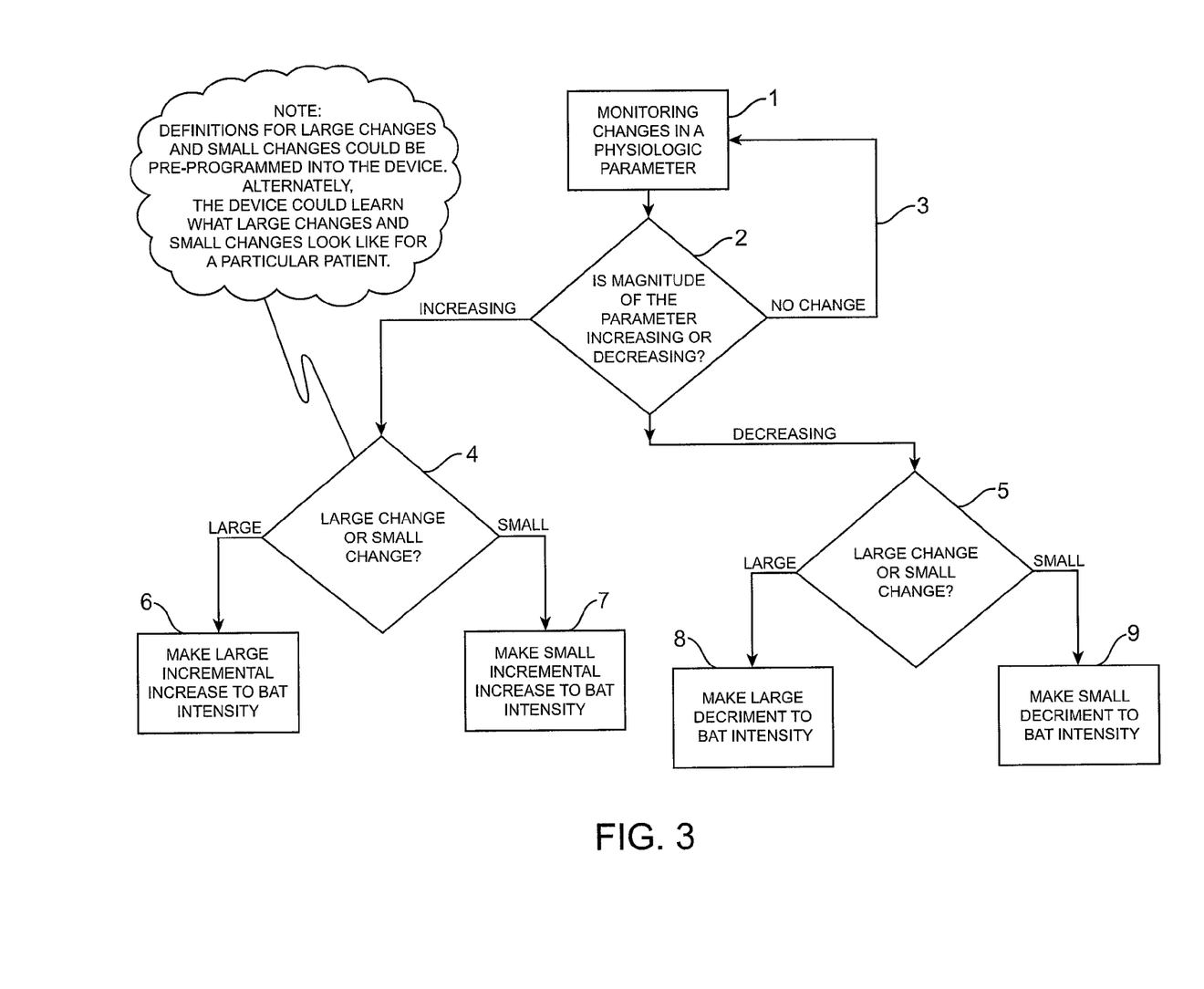
FIG. 3 is a flow diagram of a process, embodying features of the present invention.

Now referring to FIG. 3, a flow diagram illustrates a method embodying features of the present invention. As shown, a baroreflex activation therapy program having definitions and understanding of ranges of changes for a parameter responsive to a physiological condition in the patient is established. The parameter responsive to the physiological condition is monitored during therapy (box 1) and its value is checked for any change, and if a change is detected, it then determines whether the change was an increase or a decrease, from the starting point (or a target value) (box 2). If it is determined that there has been no change (line 3), the therapy continues and is monitored (box 1) as before and the parameter continues to be monitored and checked for any changes (box 2).

If it is determined that there has been an increasing change (box 2) then the method provides for identifying the nature of the increase, for example, whether it is a large or small increase (box 4). If the increase is large, the method makes a large incremental increase to the baroreflex activation therapy intensity (box 6). If the increase is small, the method makes a small incremental increase to the baroreflex activation therapy intensity (box 7).

If it is determined that there has been an decreasing change (box 2) then the method provides for identifying the nature of the decrease, for example, whether it is a large or small decrease (box 5). If the decrease is large, the method makes a large incremental decrease to the baroreflex activation therapy intensity (box 8). If the decrease is small, the method makes a small incremental decrease to the baroreflex activation therapy intensity (box 9).

Figure 4:
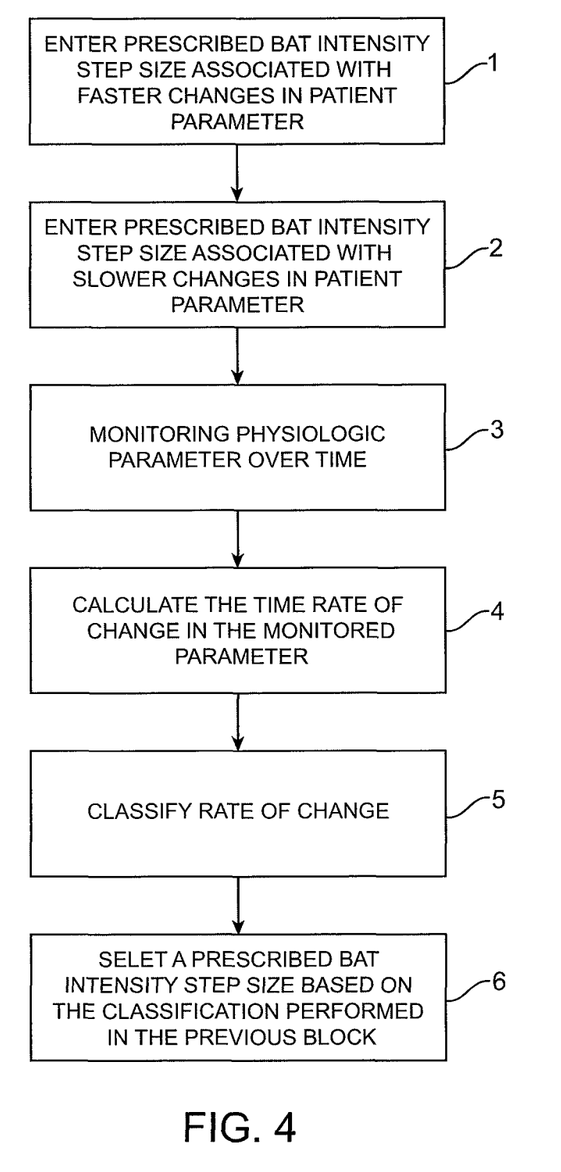
FIG. 4 is a flow diagram of a process, embodying features of the present invention.

Now referring to FIG. 4, a flow diagram illustrates a method embodying features of the present invention. As shown, in boxes 1 and 2, a prescribed baroreflex activation therapy is established by the physician (box 1) with a baroreflex activation therapy intensity step size associated with faster changes in patient parameter and intensity step size associated with slower changes in patient parameter (box 2). The parameter representative of a physiological condition is monitored (box 3) and the rate of any change in the monitored parameter is calculated (box 4). The rate of change for the parameter is classified (box 5). Thereafter, a prescribed baroreflex activation therapy intensity step size based on the classification made at the earlier step (box 5) is selected (box 6).

Figure 5:
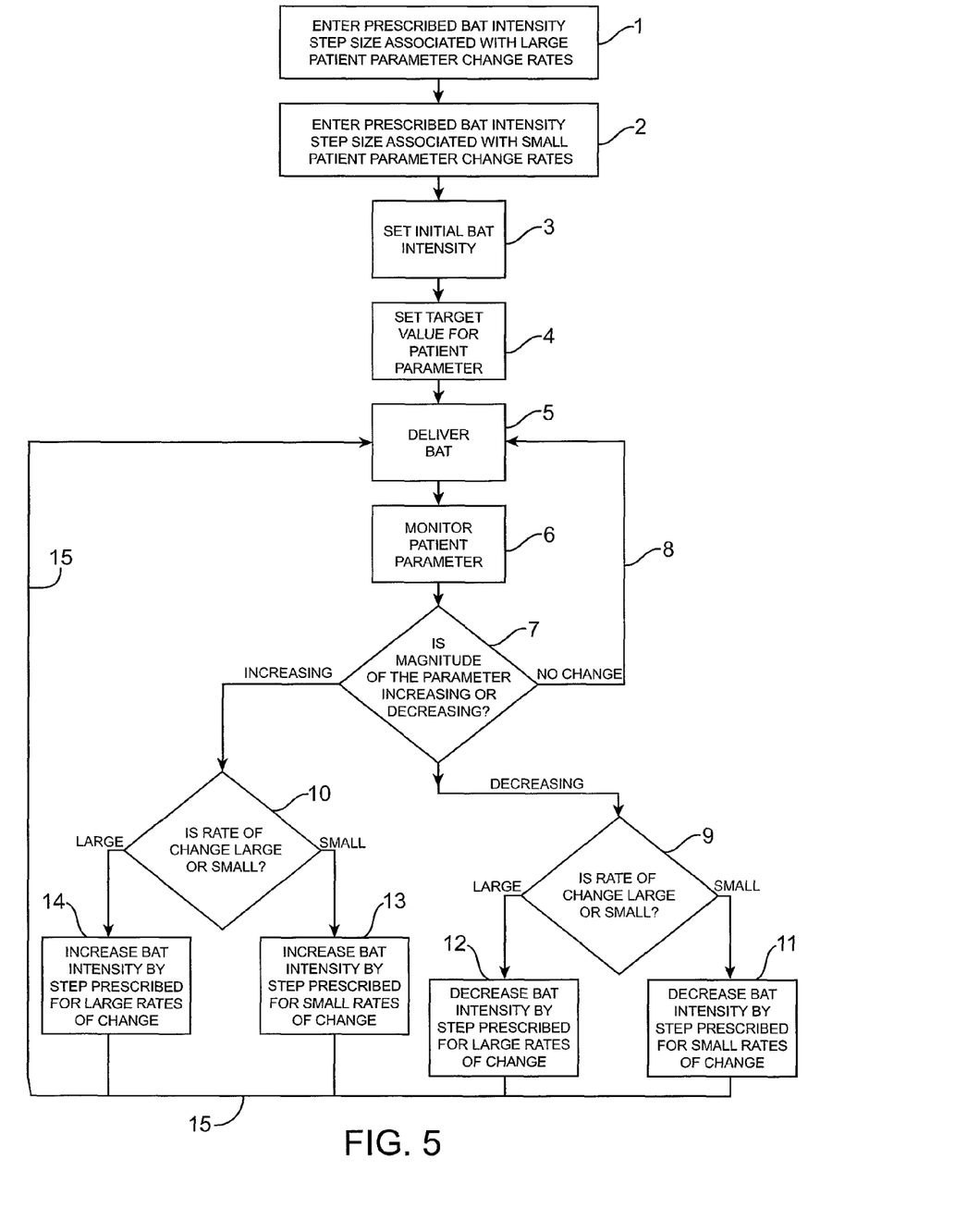
FIG. 5 is a flow diagram of a process, embodying features of the present invention.

Now referring to FIG. 5, a flow diagram illustrates a method embodying features of the present invention. As shown a prescribed baroreflex activation therapy intensity step sizes associated with large and small patient parameter changes are established and programmed into the system (box 1 and 2). The initial baroreflex activation therapy intensity is established (box 3) as well as a target value for a patient parameter (box 4). Baroreflex activation therapy is delivered to the patient (box 5), while the parameter is being monitored (box 6). It is determined whether there has been a change in the magnitude of the parameter and if so, whether such change is an increase or decrease (box 7). If there has been no change (line 8), the baroreflex activation therapy continues (box 5) as before with the parameter being monitored for any changes in its magnitude (box 6).

If it is determined that there has been a decreasing change (box 7) then the method provides for identifying what the rate of change has been (box 9) (e.g., large or small). If the rate of change is determined to have been large, baroreflex activation therapy intensity is decreased by step prescribed for large rates of change (box 12). If the rate of change is determined to have been small, baroreflex activation therapy intensity is decreased by step prescribed for small rates of change (box 11). Thereafter, the baroreflex activation therapy continues (line 15) under the new regimen (box 5) and the parameter continues to be measured (box 6).

If it is determined that there has been an increasing change (box 7) then the method provides for identifying the what the rate of change has been (box 10) (e.g., large or small). If the rate of change is determined to have been large, baroreflex activation therapy intensity is increased by step prescribed for large rates of change (box 14). If the rate of change is determined to have been small, baroreflex activation therapy intensity is increased by step prescribed for small rates of change (box 13). Thereafter, the baroreflex activation therapy continues (line 15) under the new regimen (box 5) and the parameter continues to be measured (box 6).

Figure 6:
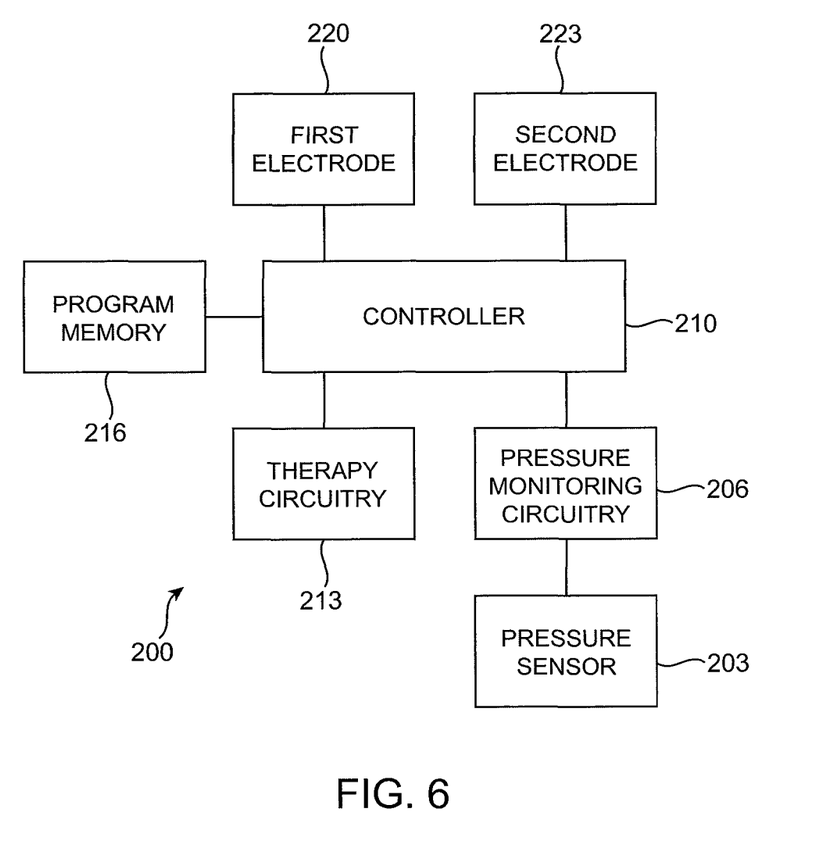
FIG. 6 a block diagram of a baroreflex activation therapy system, embodying features of the present invention.

With reference to FIG. 6, in one embodiment a system 200 for activation/stimulation of the baroreflex system of a patient is shown. The system 200 includes a pressure sensor 203 connected to a pressure monitoring circuitry 206 which in turn is connected to a controller 210. A therapy circuitry 213 is also connected to the controller 210. A memory 216 is connected to the controller and which provides the instruction and therapy algorithm to the controller 210. Electrode assemblies, 220 and 230 are connected at one end to the controller and at another end to the patient to provide baroreflex stimulation to the patient's baroreflex system.

Figure 7:
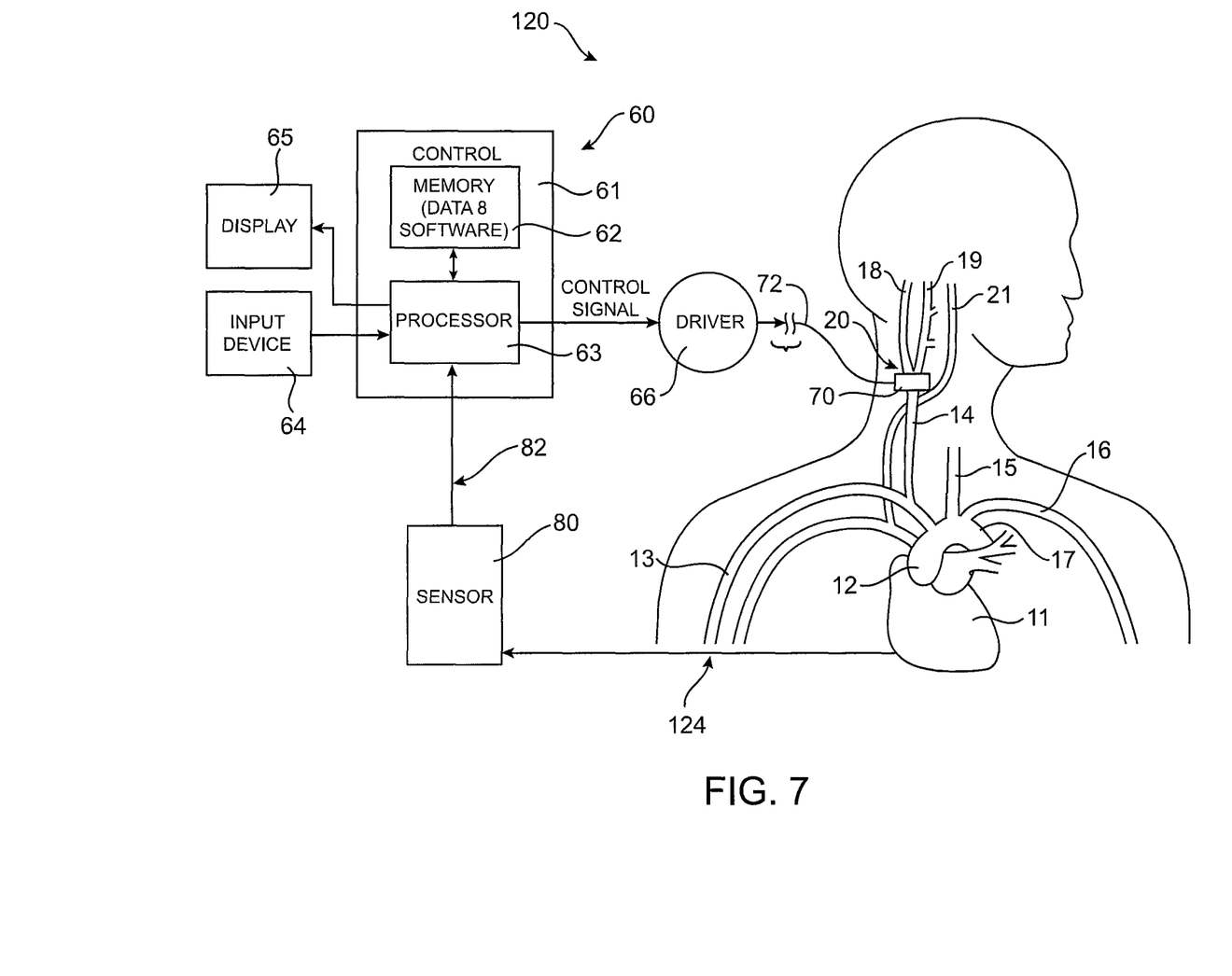
FIG. 7 is a flow diagram of a baroreflex activation therapy system for, embodying features of the present invention.

Now referring to FIG. 7, the general features of a baroreflex activation system usable in the practice of the present invention and incorporating one or more features of the present invention is shown. The system may be modified to include any one or more features of the present invention. The system 120 includes a processor 63, a baroreflex activation device 70, and a sensor 80. For clarity, the sensor 80 is shown as one unit located outside the patient, such as would be the case if the sensor 80 comprised an external electrocardiogram (ECG) device. In alternative embodiments, however, the sensor 80 (or multiple sensors) may be located on or in the heart 11 or in any other suitable location within the patient. Optionally, processor 63 may be part of a control system 60, which may include a control block 61 (housing processor 63 and memory 62), a display 65 and/or and input device 64. Processor 63 is coupled with sensor 80 by an electric sensor cable or lead 82 and to baroreflex activation device 70 by an electric control cable 72. (In alternative embodiments, lead 82 may be any suitable corded or remote connection means, such as a remote signaling device.) Thus, processor 63 receives a sensor signal from sensor 80 by way of sensor lead 82 and transmits a control signal to baroreflex activation device 70 by way of control cable 72. In an alternative embodiment, the processor 63 may be combined in one unitary device with the baroreflex activation device 70.

As discussed above, in one embodiment, generally, the heart 11 may be coupled with the sensor 80 by way of one or more leads 124, such as with an ECG device. In other embodiments, the sensor(s) 80 may be attached directly to a wall of the heart 11 or to any other suitable anatomical structure.

As mentioned above, the sensor 80 generally senses and/or monitors one or more parameters, such as but not limited to change in heart rate, change in cardiac pressure(s), change in contraction timing of one or both atria and ventricles of the heart, change in electrocardiogram shape (such as T-wave shape), change in blood pressure and/or the like. The parameter sensed by sensor 80 is then transmitted to processor 63, which may generate a control signal as a function of the received sensor signal. A control signal will typically be generated, for example, when a sensor signal is determined to be indicative of physiological condition of the patient. If decreased cardiac efficiency, for example, is determined to be an advance indicator of the onset of heart failure, data that is sensed and processed and determined to be indicative of decreased efficiency will cause processor 63 to generate a control signal. The control signal activates, deactivates, modifies the intensity or timing of, or otherwise modulates baroreflex activation device 70. In some embodiments, for example, baroreflex activation device 70 may activate an ongoing baroreflex at a constant rate until it receives a control signal, which may cause the device 70 to either increase or decrease intensity of its baroreflex activation. In another embodiment, baroreflex activation device 70 may remain in a turned-off mode until activated by a control signal from processor 63. In another embodiment, when sensor 80 detects a parameter indicative of normal body function (e.g., steady heart rate and/or steady intracardiac pressures), processor 63 generates a control signal to modulate (e.g., deactivate) baroreflex activation device 70. Any suitable combination is contemplated in various embodiments.

Again, sensor 80 may comprise any suitable device that measures or monitors a parameter indicative of the need to modify baroreflex activation and. For example, sensor 80 may comprise a physiologic transducer or gauge that measures cardiac activity, such as an ECG, or any other physiologic activity described above. Alternatively, sensor 80 may measure cardiac activity by any other technique, such as by measuring changes in intracardiac pressures or the like. Examples of suitable transducers or gauges for sensor 80 include ECG electrodes and the like. Although only one sensor 80 is shown, multiple sensors 80 of the same or different type at the same or different locations may be utilized. Sensor 80 is preferably positioned on or near the patient's heart, one or near major vascular structures such as the thoracic aorta, or in another suitable location to measure cardiac activity, such as increased heart rate or pressure changes. Sensor 80 may be disposed either inside or outside the body in various embodiments, depending on the type of transducer or gauge utilized. Sensor 80 may be separate from baroreflex activation device 70, as shown schematically in FIG. 6, or may alternatively be combined therewith in one device.

The baroreflex activation component of the baroreflex activation device 70 may comprise a wide variety of devices which utilize mechanical, electrical, thermal, chemical, biological, or other means to activate baroreceptors 30 and/or other tissues In many embodiments, particularly the mechanical activation embodiments, the baroreflex activation device 70 indirectly activates one or more baroreceptors 30 by stretching or otherwise deforming the vascular wall 40 surrounding baroreceptors 30. In some other instances, particularly the non-mechanical activation embodiments, baroreflex activation device, device 70 may directly activate one or more baroreceptors 30 by changing the electrical, thermal or chemical environment or potential across baroreceptors 30. It is also possible that changing the electrical, thermal or chemical potential across the tissue surrounding baroreceptors 30 may cause the surrounding tissue to stretch or otherwise deform, thus mechanically activating baroreceptors 30. In other instances, particularly the biological activation embodiments, a change in the function or sensitivity of baroreceptors 30 may be induced by changing the biological activity in baroreceptors 30 and altering their intracellular makeup and function.

Many embodiments of the baroreflex activation device 70 is suitable for implantation, and is preferably implanted using a minimally invasive percutaneous translumenal approach and/or a minimally invasive surgical approach, depending on whether the device 70 is disposed intravascularly, extravascularly or within the vascular wall 40. The baroreflex activation device 70 may be positioned anywhere baroreceptors 30 affecting baroreflex system 50 are numerous, such as in the heart 11, in the aortic arch 12, in the common carotid arteries 18/19 near the carotid sinus 20, in the subclavian arteries 13/16, or in the brachiocephalic artery 22. The baroreflex activation device 70 may be implanted such that the device 70 is positioned immediately adjacent baroreceptors 30. Alternatively, the device 70 may be positioned in the low-pressure side of the heart or vasculature, near a baroreceptor, as described in U.S. patent application Ser. No. 10/284,063, previously incorporated by reference. In fact, the baroreflex/CRT device 70 may even be positioned outside the body such that the device 70 is positioned a short distance from but proximate to baroreceptors 30. In one embodiment, the baroreflex activation device 70 is implanted near the right carotid sinus 20 and/or the left carotid sinus (near the bifurcation of the common carotid artery) and/or the aortic arch 12, where baroreceptors 30 have a significant impact on baroreflex system 50. For purposes of illustration only, the present invention is described with reference to the baroreflex activation device 70 positioned near the carotid sinus 20.

Memory 62 may contain data related to the sensor signal, the control signal, and/or values and commands provided by input device 64. Memory 62 may also include software containing one or more algorithms defining one or more functions or relationships between the control signal and the sensor signal. The algorithm may dictate activation or deactivation control signals depending on the sensor signal or a mathematical derivative thereof. The algorithm may dictate an activation or deactivation control signal when the sensor signal falls below a lower predetermined threshold value, rises above an upper predetermined threshold value or when the sensor signal indicates the occurrence of a specific physiological event.

As mentioned previously, the baroreflex activation device 70 may activate baroreceptors 30 mechanically, electrically, thermally, chemically, biologically or otherwise. However, it is generally contemplated that the control signal that energizes baroreflex activation device 70 will be an electrical signal. In some instances, control system 60 includes a driver 66 to provide the desired power mode for the baroreflex activation device 70. For example if the baroreflex activation device 70 utilizes pneumatic or hydraulic actuation, driver 66 may comprise a pressure/vacuum source and the cable 72 may comprise fluid line(s). If the baroreflex activation device 70 utilizes electrical or thermal actuation, driver 66 may comprise a power amplifier or the like and the cable 72 may comprise electrical lead(s). If baroreflex activation device 70 utilizes chemical or biological actuation, driver 66 may comprise a fluid reservoir and a pressure/vacuum source, and cable 72 may comprise fluid line(s). In other instances, driver 66 may not be necessary, particularly if processor 63 generates a sufficiently strong electrical signal for low level electrical or thermal actuation of baroreflex activation device 70.

Control system 60 may operate as a closed loop utilizing feedback from sensor 80, or as an open loop utilizing commands received by input device 64. The open loop operation of control system 60 preferably utilizes some feedback from sensor 80, but may also operate without feedback. Commands received by the input device 64 may directly influence the control signal or may alter the software and related algorithms contained in memory 62. The patient and/or treating physician may provide commands to input device 64. Display 65 may be used to view the sensor signal, control signal and/or the software/data contained in memory 62.

The control signal generated by control system 60 may be continuous, periodic, episodic or a combination thereof, as dictated by an algorithm contained in memory 62. The algorithm contained in memory 62 defines a stimulus regimen which dictates the characteristics of the control signal as a function of time, and thus dictates baroreflex activation as a function of time. Continuous control signals include a pulse, a train of pulses, a triggered pulse and a triggered train of pulses, all of which are generated continuously. Examples of periodic control signals include each of the continuous control signals described above which have a designated start time (e.g., beginning of each minute, hour or day) and a designated duration (e.g., 1 second, 1 minute, 1 hour). Examples of episodic control signals include each of the continuous control signals described above which are triggered by an episode (e.g., activation by the patient/physician, an increase in blood pressure above a certain threshold, etc.).

The stimulus regimen governed by control system 60 may be selected to promote long term efficacy. It is theorized that uninterrupted or otherwise unchanging activation of baroreceptors 30 may result in the baroreceptors and/or the baroreflex system becoming less responsive over time, thereby diminishing the long-term effectiveness of the therapy. Therefore, the stimulus regimen may be selected to activate, deactivate or otherwise modulate baroreflex activation device 70 in such a way that therapeutic efficacy is maintained long term. For purposes of clarity, it should be mentioned that the term stimulation and activation may be used interchangeable as well as the terms therapy and stimulus regimen. A therapy may, comprise, a plurality of does regiments or regimens for delivery of different doses/intensities.

In addition to maintaining therapeutic efficacy over time, the stimulus regimens of the present invention may be selected to reduce power requirement/consumption of control system 60. As will be described in more detail, the stimulus regimen may dictate that baroreflex activation device 70 be initially activated at a relatively higher energy and/or power level, and subsequently activated at a relatively lower energy and/or power level. The first level attains the desired initial therapeutic effect, and the second (lower) level sustains the desired therapeutic effect long term. By reducing the energy and/or power level after the desired therapeutic effect is initially attained, the power required or consumed by the device 70 is also reduced long term. This may correlate into systems having greater longevity and/or reduced size (due to reductions in the size of the power supply and associated components).

Another advantage of the stimulus regimens of the present invention is the reduction of unwanted collateral tissue stimulation. As mentioned above, the stimulus regimen may dictate that baroreflex activation device 70 be initially activated at a relatively higher energy and/or power level to attain the desired effect, and subsequently activated at a relatively lower energy and/or power level to maintain the desired effect. By reducing the output energy and/or power level, the stimulus may not travel as far from the target site, thereby reducing the likelihood of inadvertently stimulating adjacent tissues such as muscles in the neck and head.

The stimulus regimens described herein may be applied to baropacing (i.e., electrical stimulation of the carotid sinus nerve), as in the baropacing system disclosed in U.S. Pat. No. 6,073,048 to Kieval et al., the entire disclosure of which is incorporated herein by reference.

In a representative embodiment, the stimulus regimen is represented by pulse frequency, for example in the order of 20 Hz (Hertz), a corresponding pulse every 50 ms can be less than 1 ms, $\Delta 1$ is 30-250 Vs (microseconds), $\Delta 2$ and $\Delta 3$ are at least 30 vs. For example, a charge balance interval CBW can be set at 8±2 ms. A nominal heart rate is 1-1.2 Hz (burst interval of 0.83-1 second), so a representative burst interval might comprise 6-8 pulses at 20 Hz over the first 250-350 ms followed by no pulses or pulses at a lower frequency over the remainder of the burst interval. These numbers are exemplary and are by no means critical.

The stimulus regimens including a baroreflex activation therapy intensity may be increased or decreased by a predetermined small or large step-size associated with a change in a monitored parameter or a need to otherwise adjust or modify therapy. If for example, a need to reduce therapy is determined, a therapy can be reduced in small or large increments based on the need to reduce in such small or large increments. If for example a need to increase therapy is determined, a therapy can be increased in small or large increments based on the need to increase in small or large increments. Accordingly, the initiation of therapy may be delivered in small increments so as to gauge a patient's response to a therapy. If a need to reduce therapy is determined (by way of example when a patient needs to have therapy paused for a battery change or some other reason), a therapy can be reduced by reducing the amplitude in small or large increments, such as reducing the current or voltage of the therapy. Such current or voltage may be reduced for example in small increments of about 0.1 to 1 volt or 1-2 Hz per day for 7-14 days depending on the patient's response to the reduction of therapy. In a representative embodiment of small increments, in a patient receiving a programmed therapy of 5.5 volts, the therapy may be reduced from 5.5 volts to 0.1 volt over a period of 7-10 days. In a representative embodiment, in a patient receiving a programmed therapy of 20 Hz, the therapy may be reduced from 20 Hz to 10 Hz over a period of 7-10 days. Therapy may be reduced in larger increments, such as in larger current or voltage drops over a shorter time, although it should be understood that "large" and "small" increments may be defined differently for different patients.

The stimulus regimen may be described in terms of the control signal and/or the output signal from baroreflex activation device 70. Generally speaking, changes in the control signal result in corresponding changes in the output of baroreflex activation device 70 which affect corresponding changes in baroreceptors 30. The correlation between changes in the control signal and changes in baroreflex activation device 70 may be proportional or disproportional, direct or indirect (inverse), or any other known or predictable mathematical relationship. For purposes of illustration only, the stimulus regimen may be described herein in such a way that assumes the output of baroreflex activation device 70 is directly proportional to the control signal. Further details of exemplary stimulus regimens may be found, for example, in U.S. Patent Application No. 60/584,730, which was previously incorporated by reference.

Control system 60 may be implanted in whole or in part. For example, the entire control system 60 may be carried externally by the patient utilizing transdermal connections to the sensor lead 82 and the control lead 72. Alternatively, control block 61 and driver 66 may be implanted with input device 64 and display 65 carried externally by the patient utilizing transdermal connections therebetween. As a further alternative, the transdermal connections may be replaced by cooperating transmitters/receivers to remotely communicate between components of control system 60 and/or sensor 80 and baroreflex activation device 70.

For further details of exemplary baroreflex activation devices, reference may be made to U.S. Pat. Nos. 6,522,926 and 6,616,624, and U.S. patent application Ser. Nos. 09/964,079, 09/963,777, 09/963,991, 10/284,063, 10/453,678, 10/402,911, 10/402,393, 10/818,738, and 60/584,730, which were previously incorporated by reference.

Although the above description provides a complete and accurate representation of the invention, the present invention may be manifested in a variety of forms other than the specific embodiments described and contemplated herein. Accordingly, departures in form and detail may be made without departing from the scope and spirit of the present invention as described in the appended claims

What is claimed is:

1. A method for treating a patient, comprising:
    activating a baroreflex system of the patient with a baroreflex activation device according to a baroreflex activation therapy, the therapy stored within a control system coupled to the baroreflex activation device;
    establishing an initial target value for a physiological parameter of the patient;
    monitoring the physiological parameter;
    using the control system to determine whether the value of the physiological parameter has changed and if so, automatically performing the following steps with the control system:
        determining whether the value of the physiological parameter has increased or decreased as compared to the initial target value of the physiological parameter;
        determining a magnitude of the change of the physiological parameter; and
        determining a rate of change of the physiological parameter over a period of time; and
    adjusting the baroreflex activation therapy in response to at least one of the magnitude of the change of the monitored parameter or the rate of change of the monitored physiological parameter.

2. The method of claim 1, wherein the magnitude of a change for the physiological parameter affects adjusting of the baroreflex activation therapy.

3. The method of claim 2, wherein if an increase in the magnitude of the monitored physiological parameter is determined to be a member of a class of large changes, then the baroreflex activation therapy is increased by a predetermined large step-size associated with large changes in the monitored physiologic parameter.

4. The method of claim 2, wherein if an increase in the magnitude of the monitored physiological parameter is determined to be a member of a class of small changes, then the baroreflex activation therapy is increased by a predetermined small step-size associated with small changes in the monitored physiologic parameter.

5. The method of claim 2, wherein if a decrease in the magnitude of the monitored physiological parameter is determined to be a member of a class of large changes, then the baroreflex activation therapy is decreased by a predetermined large step-size associated with large changes in the monitored physiologic parameter.

6. The method of claim 2, wherein if a decrease in the magnitude of the monitored physiological parameter is determined to be a member of a class of small changes, then the baroreflex activation therapy is decreased by a predetermined small step-size associated with small changes in the monitored physiologic parameter.

7. The method of claim 1, further comprising determining a baroreflex activation therapy intensity step size associated with a class of change in the monitored physiological parameter magnitude.

8. The method of claim 7, further comprising creating a classification system based on data collected regarding the magnitudes of the monitored physiological parameter monitored over time.

9. A method for treating a patient, comprising:
    identifying a parameter indicative of a physiological condition of the patient;
    establishing an initial target value for the parameter;
    establishing a baroreflex activation therapy comprising a plurality of prescribed intensity step-sizes, each intensity step-size being associated with a predetermined class of parameter change rate;
    activating a baroreflex system of the patient with a baroreflex activation device according to the baroreflex activation therapy at a pre-determined intensity;
    monitoring the parameter;
    determining whether the value of the parameter has changed and if so, performing the following steps:
        determining whether the value of the parameter has increased or decreased as compared to the initial target value of the parameter;
        determining a magnitude of the change of the parameter; and
        determining a rate of change for the parameter; and
    adjusting the baroreflex activation therapy in response to at least one of the magnitude of the change of the monitored parameter or the rate of change in the class of the monitored parameter.

10. The method of claim 9, wherein if there has been no change to the value of the parameter, baroreflex activation therapy continues.

11. The method of claim 9, wherein adjusting the baroreflex activation therapy is proportional to the change in the monitored parameter.

12. The method of claim 9, wherein adjusting in the baroreflex activation therapy is unproportional to the change in the monitored parameter.

13. The method of claim 9, wherein the intensity is changed based on a prescribed step-size intensity commensurate with the magnitude of change of the parameter and rate of change of the parameter.

14. The method of claim 9, wherein if the magnitude of the parameter has increased at a large rate, then the baroreflex activation therapy intensity is increased according to the prescribed step-sized intensity commensurate with a class of large rates of change for the parameter.

15. The method of claim 9, wherein if the magnitude of the parameter has increased at a small rate, then the baroreflex activation therapy intensity is increased according to the prescribed step-sized intensity commensurate with a class of small rates of change for the parameter.

16. The method of claim 9, wherein if the magnitude of the parameter has decrease at a large rate, then the baroreflex activation therapy intensity is decreased according to the prescribed step-sized intensity commensurate with a class of large rates of change for the parameter.

17. The method of claim 9, wherein if the magnitude of the parameter has decreased at a small rate, then the baroreflex activation therapy intensity is decreased according to the prescribed step-sized intensity commensurate with a class of small rates of change for the parameter.

18. The method of claim 1, further comprising:
classifying the rate of change of the parameter; and
adjusting the baroreflex activation therapy by a prescribed therapy intensity step-size based on the classification of the rate of change of the parameter.

19. The method of claim 9, further comprising:
classifying the rate of change of the parameter; and
adjusting the baroreflex activation therapy by the prescribed therapy intensity step-size based on the classification of the rate of change of the parameter.

\* \* \* \* \*